(12) United States Patent
Umeda et al.

(10) Patent No.: US 10,390,710 B2
(45) Date of Patent: Aug. 27, 2019

(54) ELECTRONIC SPHYGMOMANOMETER FOR MEASURING BLOOD PRESSURE AND PULSE

(71) Applicants: Shota Umeda, Shiga (JP); Yukiya Sawanoi, Nara (JP); Naomi Matsumura, Osaka (JP); Tsuyoshi Kitagawa, Kyoto (JP)

(72) Inventors: Shota Umeda, Shiga (JP); Yukiya Sawanoi, Nara (JP); Naomi Matsumura, Osaka (JP); Tsuyoshi Kitagawa, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 757 days.

(21) Appl. No.: 13/749,039

(22) Filed: Jan. 24, 2013

(65) Prior Publication Data

US 2013/0190629 A1    Jul. 25, 2013

(30) Foreign Application Priority Data

Jan. 25, 2012   (JP) .................................. 2012-012737

(51) Int. Cl.
*A61B 5/02*     (2006.01)
*A61B 5/00*     (2006.01)
(Continued)

(52) U.S. Cl.
CPC ................ *A61B 5/02* (2013.01); *A61B 5/021* (2013.01); *A61B 5/024* (2013.01); *A61B 5/0235* (2013.01);
(Continued)

(58) Field of Classification Search
CPC . A61B 5/021; A61B 5/02225; A61B 5/02233; A61B 5/0235; A61B 5/024;
(Continued)

(56) References Cited

U.S. PATENT DOCUMENTS 5,309,916 A  *  5/1994  Hatschek ...................... 600/485
5,497,779 A  *  3/1996  Takaya ................... A61B 5/021
                                                          600/485

(Continued)

OTHER PUBLICATIONS

Minami et al., "Effects of Smoking Cessation on Blood Pressure and Heart Rate Variability in Habitual Smokers," Hypertension, Journal of the American Heart Association, Jan. 1999, pp. 586-590 (6 pages).

*Primary Examiner* — Amanda Lauritzen Moher
(74) *Attorney, Agent, or Firm* — Osha Liang LLP (57) ABSTRACT

An electronic sphygmomanometer includes a cuff including an air bladder, a pressure sensor, an artery volume sensor, and a computation device. The computation device includes an inner pressure control section, a volume sensor signal receive section for receiving a pulse wave signal detected by the artery volume sensor, a pressure sensor signal receive section for receiving a pressure pulse wave signal superimposed on the inner pressure of the air bladder and detected by the pressure sensor, a judgment section for choosing either the pulse wave signal or the pressure pulse wave signal as a signal for calculating pulse rate of the patient during a period when the inner pressure of the air bladder is increased and/or decreased by the inner pressure control section, and a pulse rate calculation section for calculating pulse rate of the patient based on the pulse wave signal and the signal chosen by the judgment section.

10 Claims, 10 Drawing Sheets

(51) Int. Cl.
  *A61B 5/021* (2006.01)
  *A61B 5/022* (2006.01)
  *A61B 5/0235* (2006.01)
  *A61B 5/024* (2006.01)
  *A61B 5/0215* (2006.01)
  *A61B 5/0225* (2006.01)

(52) U.S. Cl.
  CPC ...... *A61B 5/02225* (2013.01); *A61B 5/02233* (2013.01); *A61B 5/02422* (2013.01); *A61B 5/7278* (2013.01); *A61B 5/742* (2013.01); *A61B 5/022* (2013.01); *A61B 5/0225* (2013.01); *A61B 5/02108* (2013.01); *A61B 5/02158* (2013.01); *A61B 5/02208* (2013.01); *A61B 5/6824* (2013.01)

(58) Field of Classification Search
  CPC . A61B 5/02422; A61B 5/6824; A61B 5/7278; A61B 5/742; A61B 5/02; A61B 5/02208; A61B 5/02158; A61B 5/0225; A61B 5/022
  USPC .................................................. 600/479, 490
  See application file for complete search history.

(56) References Cited

U.S. PATENT DOCUMENTS

| | | | | |
|---|---|---|---|---|
| 5,735,799 A | * | 4/1998 | Baba | A61B 5/021 600/485 |
| 6,228,036 B1 | * | 5/2001 | Nakanishi | A61B 5/0225 600/491 |
| 6,475,155 B2 | * | 11/2002 | Ogura | A61B 5/021 600/500 |
| 6,527,725 B1 | * | 3/2003 | Inukai et al. | 600/485 |
| 7,935,061 B1 | * | 5/2011 | Breed | A61B 5/021 600/485 |
| 2001/0037068 A1 | * | 11/2001 | Goto | A61B 5/02116 600/485 |
| 2004/0186387 A1 | * | 9/2004 | Kosuda | A61B 5/02 600/502 |
| 2004/0193061 A1 | * | 9/2004 | Sato | A61B 5/02 600/500 |
| 2005/0283083 A1 | * | 12/2005 | Lee | A61B 5/02225 600/490 |
| 2006/0122520 A1 | * | 6/2006 | Banet et al. | 600/503 |
| 2006/0195034 A1 | * | 8/2006 | Skrabal et al. | 600/485 |
| 2008/0243008 A1 | * | 10/2008 | Habu | A61B 5/02116 600/494 |
| 2010/0076328 A1 | * | 3/2010 | Matsumura | A61B 5/021 600/500 |
| 2010/0268092 A1 | * | 10/2010 | Kobayashi | A61B 5/02007 600/483 |
| 2011/0130667 A1 | * | 6/2011 | Inoue | A61B 5/02225 600/490 |
| 2011/0257540 A1 | * | 10/2011 | Sawanoi | G01G 19/50 600/494 |
| 2012/0071768 A1 | * | 3/2012 | Yamakoshi | A61B 5/021 600/493 |

* cited by examiner

ELECTRONIC SPHYGMOMANOMETER FOR MEASURING BLOOD PRESSURE AND PULSE

BACKGROUND OF THE INVENTION

1. Field of the Invention

The present invention relates to an electronic sphygmomanometer and a measuring method for blood pressure and pulse using the electronic sphygmomanometer, and particularly relates to a measuring device for measuring blood pressure and pulse by using a cuff and a method thereof.

2. Description of the Related Art

In the past, sphygmomanometers in which a cuff (air bladder) is mounted on a measurement location such as a wrist or an upper arm, and blood pressure is calculated from cuff pressure fluctuation that is transmitted from an artery, have become popular. As the sphygmomanometer used for measuring the blood pressure variation for an extended period of time, the wrist sphygmomanometer in which a cuff is mounted on the wrist may reduce the burden on a patient compared to that in which the cuff is mounted on an upper arm. It could be said that the radial artery at the wrist is a better suited location for measuring the pulse because the artery is at a shallower location under the skin than the upper arm.

Therefore, a wrist sphygmomanometer may be a device for measuring blood pressure and pulse rate for an extended period of time.

As a measuring method for pulse, a method in which a volume change of an artery located in a comparatively shallow area under the skin is detected noninvasively to measure the pulse rate has been known. As a typical measuring method for the pulse rate, there is a method to measure the artery volume change by using a sensor, such as a photoelectronic sensor, an impedance sensor, or the like, that is arranged directly above and pressed against the artery in order to detect the volume of the artery.

In order to press the sensor to the skin to detect artery volume, a cuff used for measuring blood pressure can be used. When measuring the blood pressure by increasing and decreasing the pressure in the cuff, a pulse wave (pressure pulse wave) can be detected by the pressure sensor from the pressure variation that is superimposed on the air bladder of the cuff at that time.

Figure 1A:
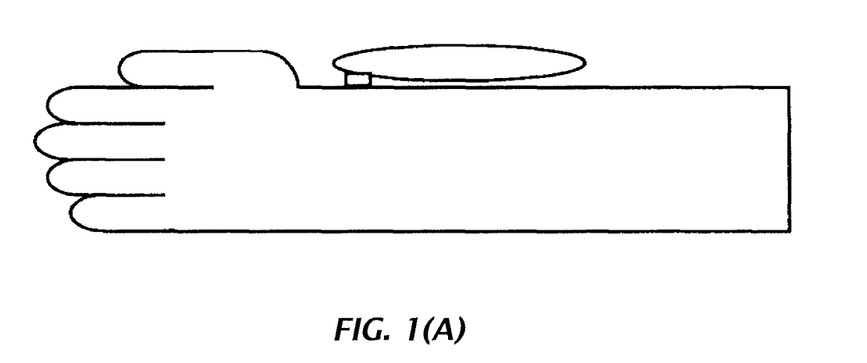
Figure 1B:
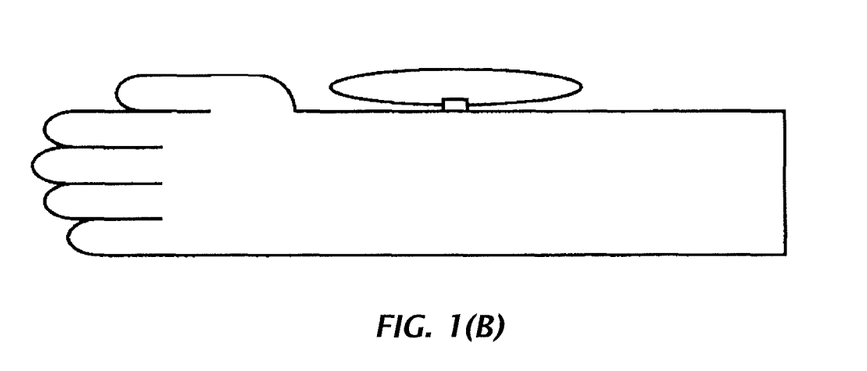
Figure 1C:
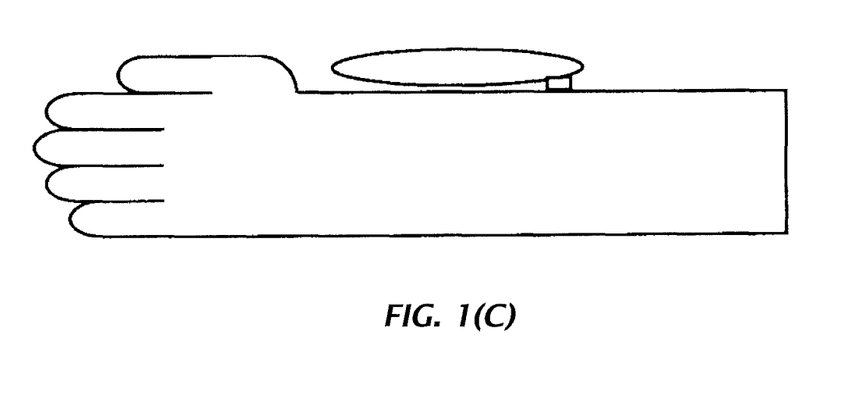

FIGS. 1 (A) to (C) are drawings illustrating positional relationships of a sensor that detects an artery volume and a cuff. In other words, FIG. 1 (A) illustrates a case where the sensor that detects the artery volume is arranged at a downstream side of the artery compared to the compressed area by the cuff, FIG. 1 (B) illustrates a case where the sensor that detects the artery volume is arranged roughly in the center of the compressed area by the cuff, and FIG. 1 (C) illustrates a case where the sensor that detects the artery volume is arranged at an upstream side of the artery compared to the cuff compressed area.

Figure 2:
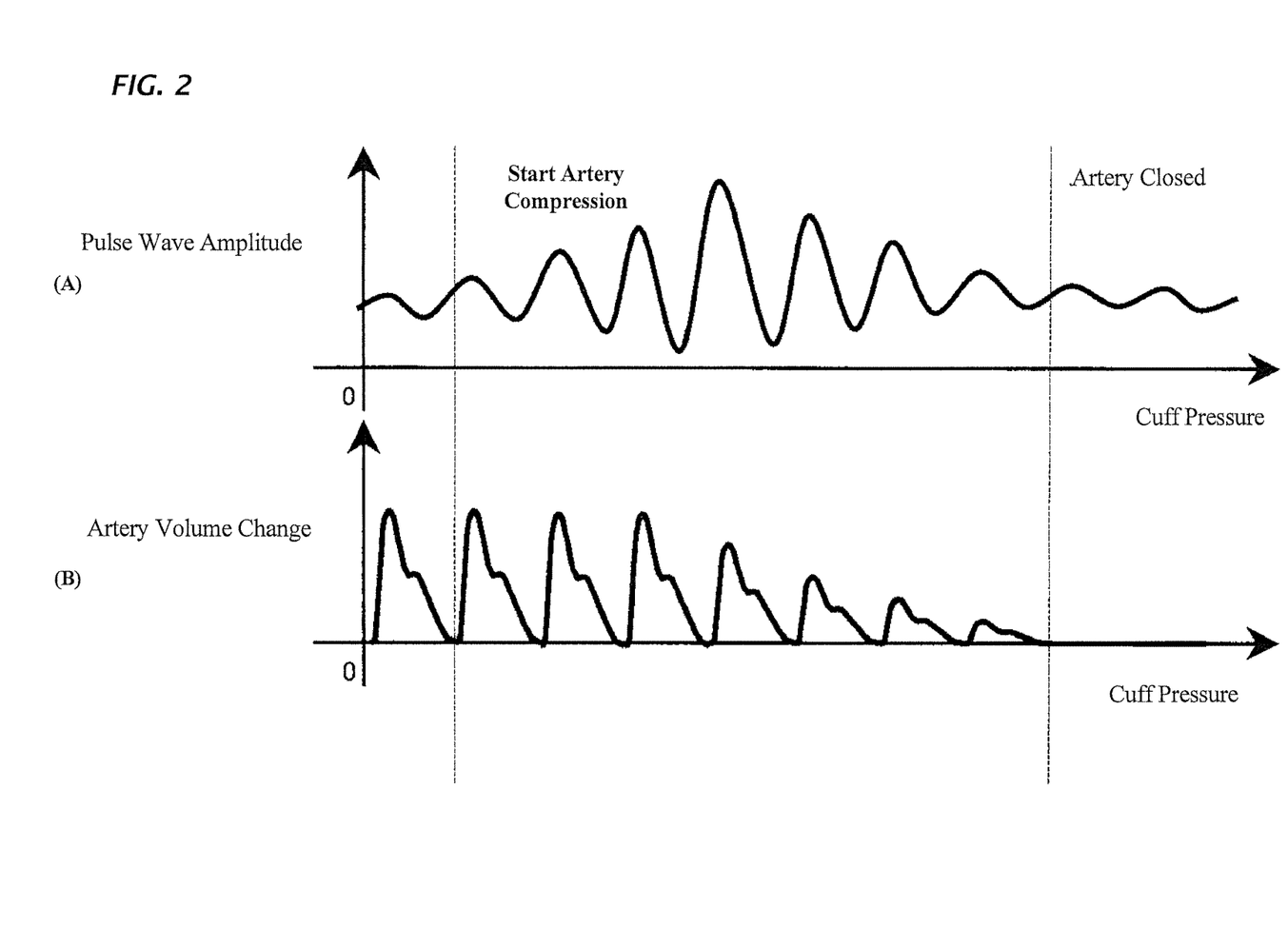
FIG. 2 is a graph illustrating a relationship between a change in the amplitude of a pulse associated with a change in inner pressure of the cuff and a measurement result of a pattern of a pulse wave that was measured by the sensor that detects the artery volume arranged in the location illustrated in FIG. 1 (A).
Figure 3:
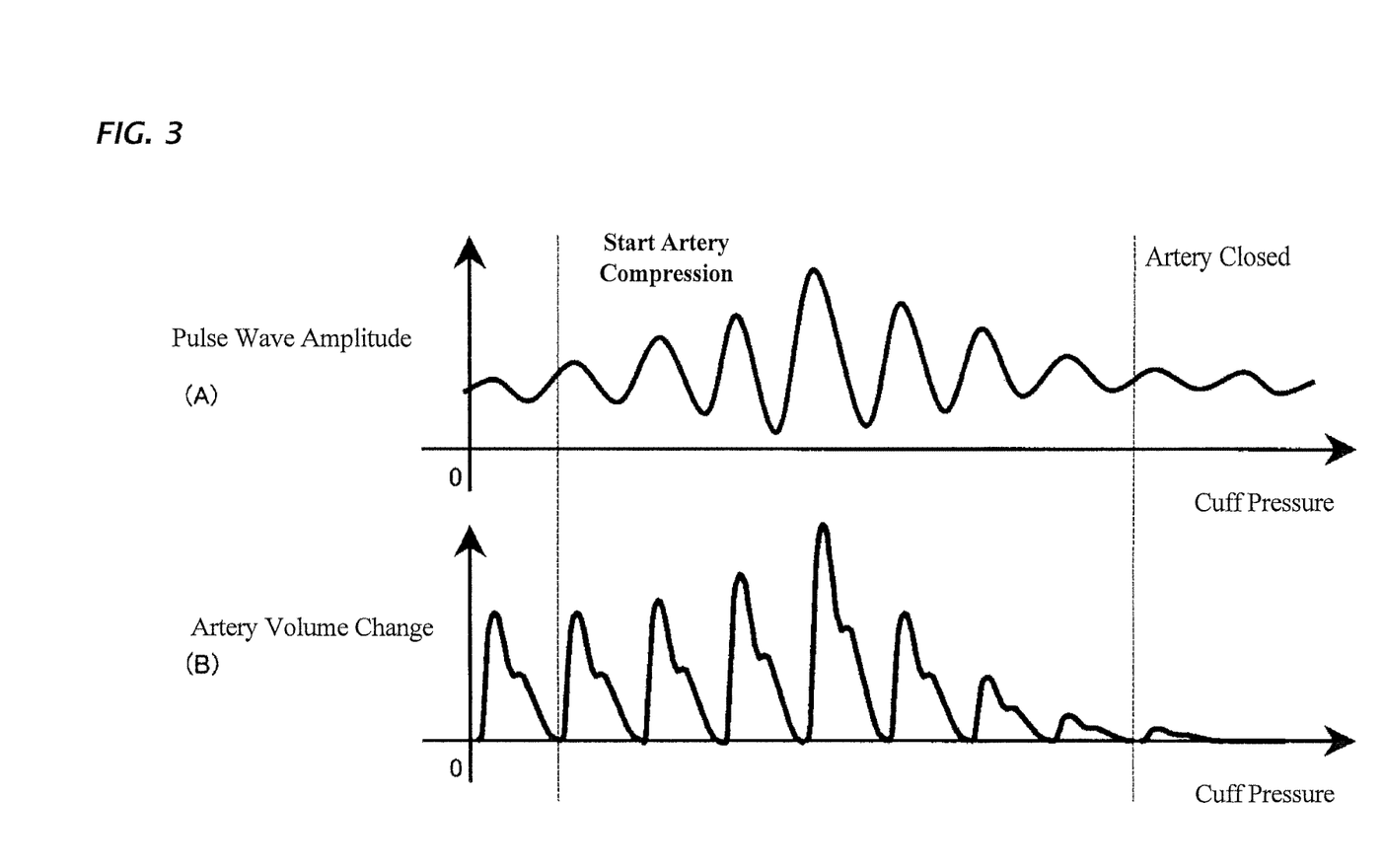
FIG. 3 is a graph illustrating a relationship between a change in the amplitude of a pulse associated with a change in inner pressure of the cuff and a measurement result of a pattern of a pulse wave that was measured by the sensor that detects the artery volume arranged in the location illustrated in FIG. 1 (B).
Figure 4:
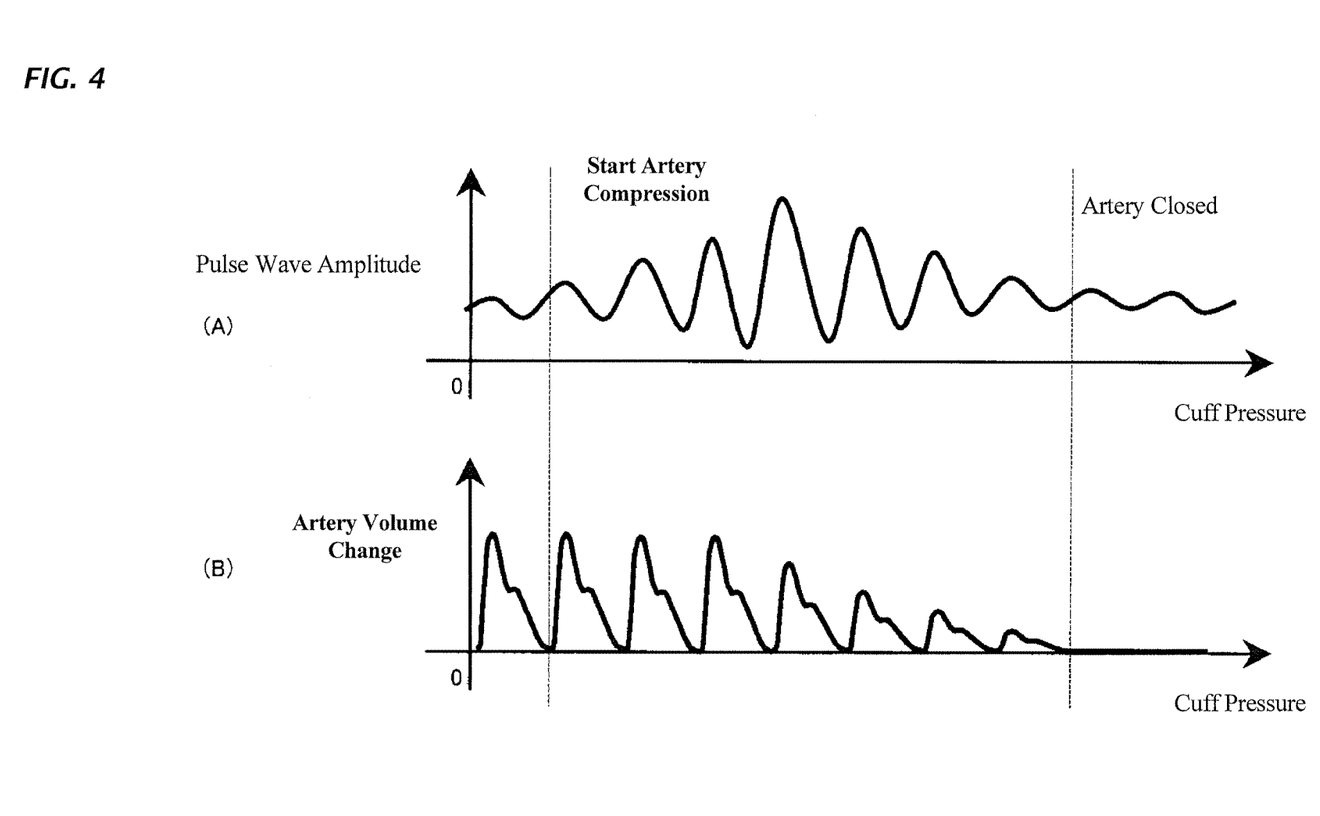
FIG. 4 is a graph illustrating a relationship between a change in the amplitude of a pulse associated with a change in inner pressure of the cuff and a measurement result of a pattern of pulse wave that was measured by the sensor that detects the artery volume arranged in the location illustrated in FIG. 1 (C).

FIG. 2 to FIG. 4 are graphs illustrating a relationship between a change in pulse amplitude associated with a change in the inner pressure of the cuff and a measurement result of a pattern of a pulse wave measured by a sensor that detects the artery volume arranged in each location illustrated in FIG. 1. In each graph, (A) illustrates a change of a pattern of the pulse wave associated with a change of an internal pressure of the cuff, (B) illustrates a measurement result of a pattern of the pulse wave measured by the sensor that detects the volume of the artery. Further, FIGS. 5 (A) and (B) are drawings illustrating a state of the sensor that detects the volume of the artery when compressing the cuff.

Figure 5A:
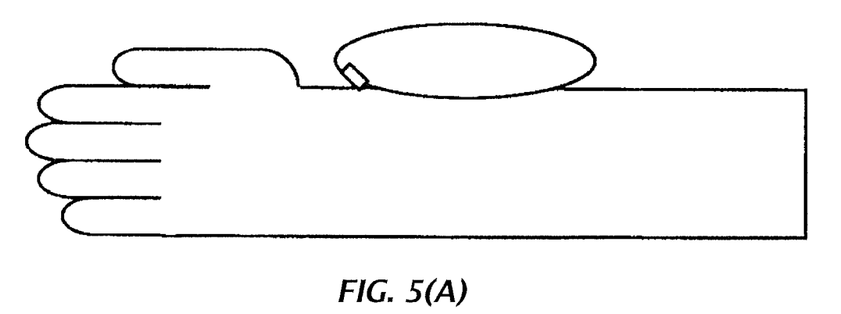

When the sensor that detects the volume of the artery is arranged at a downstream side of the artery compared to the compressed area by the cuff as illustrated in FIG. 1 (A), the pulse is no longer detected due to compression and closing of the artery by the cuff. Further, as illustrated in FIG. 5 (A), the positional relationship between the artery and the sensor that detects the volume of the artery changes in proportion to inflation of the cuff by the compression. Accordingly, as illustrated in FIG. 2, a change in the volume of the artery detected by the sensor that detects the volume of the artery is smaller in proportion to the progression of the compression and closing of the artery, and when the artery is compressed and closed, the change in volume of the artery is no longer detected.

When the sensor that detects the volume of the artery is arranged roughly in the center of the compressed area by the cuff as illustrated in FIG. 1 (B), as similar to the case in FIG. 1 (A), the pulse is no longer detected when the cuff compresses and closes the artery. Further, the change in the volume of the artery is gradually larger in proportion to the inflation of the cuff by compression due to the dynamic characteristics of the artery in this arrangement, and after the maximum value is exceeded, it gradually reduces, and when the artery is compressed and closed, the change in the volume of the artery is no longer detected.

Figure 5B:
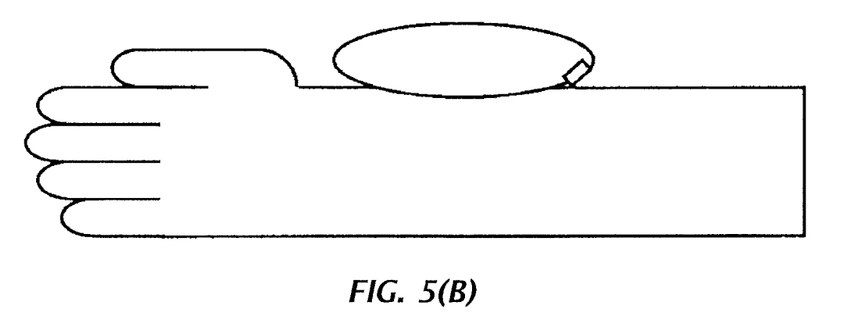

When the sensor that detects artery volume is arranged in the upstream side of the artery compared to the cuff compression area as illustrated in FIG. 1 (C), the orientation of the sensor to the measurement location to detect the volume of the artery changes due to the compression by the cuff. In other words, as illustrated in FIG. 5 (B), the propositional relationship between the artery and the sensor that detects the volume of the artery changes in proportion to inflation of the cuff by compression. Therefore, the amplitude of the pulse wave detected is reduced by the compression by the cuff.

To be more precise, as is evident from the measurements, when the sensor that detects the volume of the artery is configured so as to press against the measurement location by using the cuff used for measuring blood pressure, the amplitude of the pulse wave detected by the compression of the cuff changes and the measurement cannot be carried out accurately even by arranging the sensor that detects artery volume in any positional relationship.

SUMMARY OF THE INVENTION

Therefore, one or more embodiments of the present invention provide a measuring device and measuring method that can measure pulse rate and blood pressure value accurately for an extended period of time while reducing the burden on a patient.

One or more embodiments of the present invention relate to an electronic sphygmomanometer for measuring blood pressure and pulse rate. The electronic sphygmomanometer comprises a cuff comprising an air bladder for wrapping around a measurement location of a patient; a pressure sensor mounted on the cuff for measuring inner pressure of the air bladder; an artery volume sensor mounted on the cuff for detecting pulse wave of the patient based on a change of volume of artery; a computation device connected to the pressure sensor and artery volume sensor for calculating blood pressure and pulse rate based on the signal received from the pressure sensor and the artery volume sensor, the computation device comprising: an inner pressure control section for increasing and/or decreasing inner pressure of the air bladder at a predetermined timing; a volume sensor signal receive section for receiving a pulse wave signal detected by the artery volume sensor; a pressure sensor signal receive section for receiving a pressure pulse wave signal which is superimposed on the inner pressure of the air bladder and detected by the pressure sensor; a judgment section for choosing either one of the pulse wave signal and the pressure pulse wave signal as a signal for calculating pulse rate of the patient in accordance with a predetermined method during a period when the inner pressure of the air bladder is increased and/or decreased by the inner pressure control section; a pulse rate calculation section for calculating pulse rate of the patient based on the pulse wave signal and the signal chosen by the judgment section; and a blood pressure calculation section for calculating blood pressure based on the pressure pulse wave signal received by the pressure sensor signal receive section.

According to one or more embodiments of the present invention, a predetermined reference value is set for the pulse wave signal and the pressure pulse wave signal, respectively, and if a level of the pulse wave signal or pressure pulse wave signal is below the predetermined reference value, the signal below the reference signal level value is not chosen by the judgment section for calculating the pulse rate of the patient.

According to one or more embodiments of the present invention, the judgment section compares a signal to noise ratio value of the pulse wave signal and a signal to noise ratio value of the pressure pulse wave signal, and chooses the signal having the higher signal to noise ratio value as the signal for calculating pulse rate of the patient.

According to one or more embodiments of the present invention, the artery volume sensor is a photoelectronic sensor or an impedance sensor.

According to one or more embodiments of the present invention, the electronic sphygmomanometer is a wrist sphygmomanometer that measures the blood pressure and pulse on a wrist of the patient.

One or more embodiments of the present invention relate to a method of measuring blood pressure and pulse rate of a patient. The method comprises wrapping a cuff comprising an air bladder around an arm of a patient, wherein the cuff is provided with a pressure sensor for measuring inner pressure of the air bladder and an artery volume sensor for detecting volume of artery; detecting pulse wave signal by using the artery sensor based on the change of volume of artery; inflating and deflating the air bladder to measure blood pressure and detecting a pressure pulse wave signal by using the pressure sensor based on a change of inner pressure of the air bladder which is superimposed on the inner pressure of the air bladder during the inflation and deflation; choosing either one of the pulse wave signal and the pressure pulse wave signal as a signal for calculating pulse rate of the patient in accordance with a predetermined method during the inflation and deflation of the air bladder; and calculating pulse rate of the patient based on the pulse wave signal and the signal chosen for during the inflation and deflation of the air bladder.

According to one or more embodiments of the present invention, if a level of the detected pulse wave signal or pressure pulse wave signal is below a predetermined reference value, the signal below the reference signal level value is not chosen as the signal for calculating the pulse rate of the patient.

According to one or more embodiments of the present invention, the method further comprises comparing a signal to noise ratio value of the pulse wave signal and a signal to noise ratio value of the pressure pulse wave signal, and choosing the signal having the higher signal to noise ratio value for calculating the pulse rate of the patient.

According to one or more embodiments of the present invention, the artery volume sensor is a photoelectronic sensor or an impedance sensor.

According to one or more embodiments of the present invention, the electronic sphygmomanometer is a wrist sphygmomanometer that measures the blood pressure and pulse on a wrist of the patient.

BRIEF DESCRIPTION OF THE DRAWINGS

FIGS. 1 (A) to (C) are drawings illustrating positional relationships of a sensor that detects the artery volume and a cuff.

FIGS. 5 (A) and (B) are drawings illustrating states of the sensor that detects an artery volume when compressing the cuff.

DETAILED DESCRIPTION OF INVENTION

Embodiments of the present invention will be described hereinafter with reference to drawings. In the following descriptions, the same reference numerals are assigned to the same parts and configuration elements. Those terms and functions are also the same.

Configuration of the Device

Figure 6:
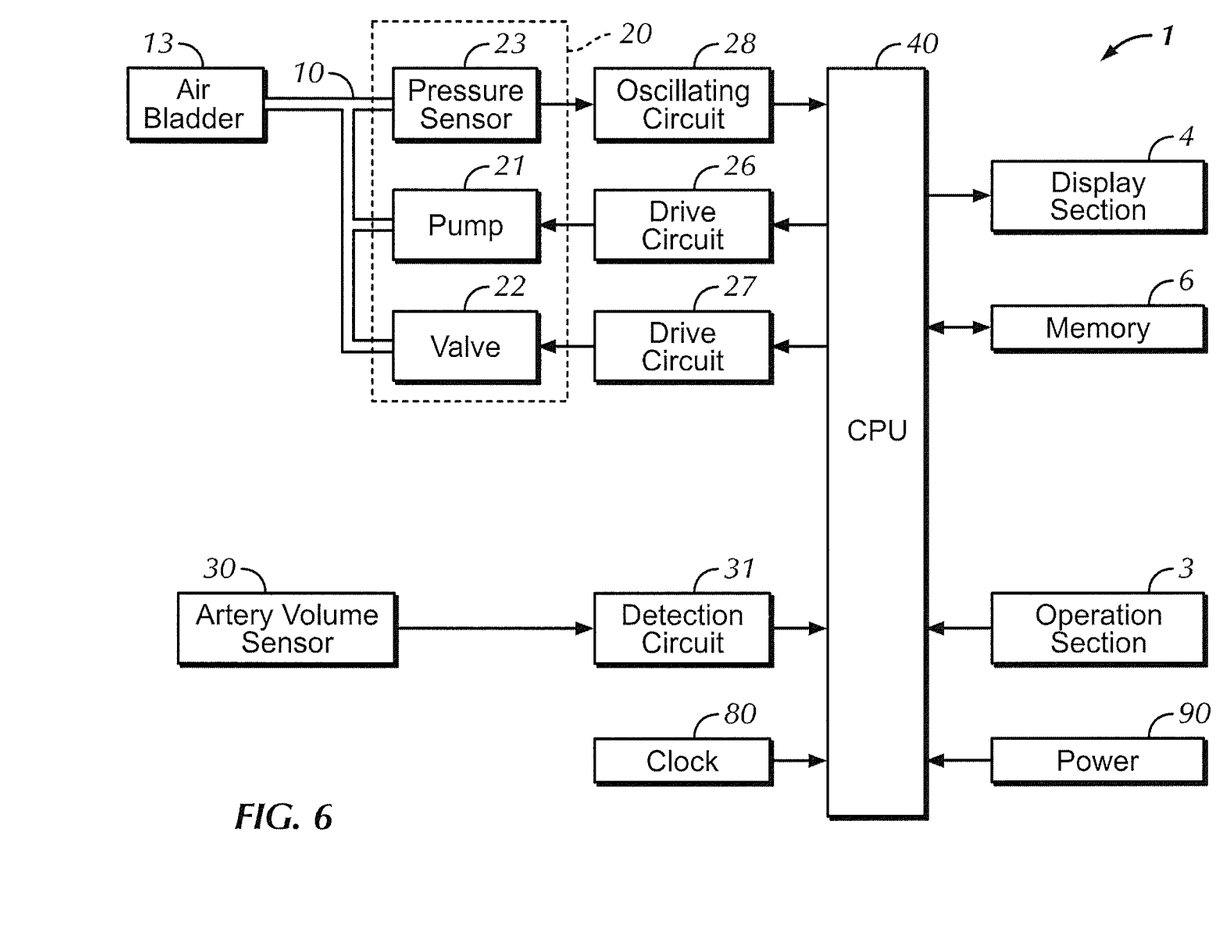
FIG. 6 is a block diagram illustrating a specific example of a device configuration of an electronic sphygmomanometer (hereinafter referred to as the sphygmomanometer) as a measurement device according to the embodiment.

FIG. 6 is a block diagram illustrating a specific example of a device configuration of an electronic sphygmomanometer (hereinafter referred to as the sphygmomanometer) as a measurement device in accordance with one or more embodiments of the present invention. The sphygmomanometer 1 is used for measuring blood pressure variation for an extended period of time. Therefore, as described above, it is assumed that a wrist sphygmomanometer in which a cuff (air bladder) is mounted on the wrist is used here. However, the sphygmomanometer is not limited to only being mounted to the wrist, and the sphygmomanometer is also able to be mounted on other locations of the four limbs such as an upper arm, an ankle or the like.

The sphygmomanometer 1 includes an air bladder 13 for measuring, and the air bladder 13 is connected to an air system 20 with an air tube 10 as illustrated in FIG. 6. The air system 20 includes a pressure sensor 23 that measures the inner pressure of the air bladder 13, a pump 21 that supplies and discharges air to the air bladder 13, and a valve 22.

The pressure sensor 23, pump 21, and valve 22 are electrically connected to an oscillating circuit 28, a drive circuit 26, and a drive circuit 27 respectively, and further, the oscillating circuit 28, drive circuit 26, and the drive circuit 27 are all electrically connected to a CPU (Central Processing Unit) 40 that controls the entire sphygmomanometer 1.

Furthermore, a display section 4, an operation section 3, a memory 6 that stores a program executed in CPU 40 as well as stores data necessary for computation, a clock 80, and a power source 90 are connected to the CPU 40.

The drive circuit 26 drives the pump 21 in accordance with a control signal from the CPU 40. Accordingly, air is injected to the air bladder 13.

The drive circuit 27 drives the valve 22 in accordance with a control signal from the CPU 40. Accordingly, the valve 22 is released and/or stopped.

The pressure sensor 23 is a pressure sensor of a capacitive-type sensor, and the capacitive value changes in accordance with the inner change of the air bladder 13. The pressure sensor 23 is connected to an oscillating circuit 28, and the oscillating circuit 28 converts to an oscillation frequency signal according to the capacitive value of the pressure sensor 23 and inputs to the CPU 40.

Further, the sphygmomanometer 1 includes an artery volume sensor 30 that detects a volume of a pulse rate as illustrated in FIG. 6. The artery volume sensor 30 is a surface that contacts the measurement location when the air bladder 13 is mounted and placed in the vicinity of directly above the artery at the time of mounting.

According to one or more embodiments of the present invention, a photoelectronic sensor including a light emitting element and a light receiving element is used for the artery volume sensor 30. An impedance sensor may be used as another option. In addition, the photoelectronic sensor and the impedance sensor may be used two or more in the artery volume sensor 30.

The artery volume sensor 30 is connected electrically to a detection circuit 31, and outputs a sensor signal to the detection circuit 31. The detection circuit 31 is connected electrically to the CPU 40, and converts the inputted sensor signal to a voltage value and inputs to the CPU 40.

Outline of the Operation

In the sphygmomanometer 1, a blood pressure value is calculated and also a pulse rate is calculated. When the artery is not compressed by the air bladder 13, in other words, at a timing other than during the operation of measuring blood pressure, a pulse rate is detected by the artery volume sensor 30. When the artery is compressed by the air bladder 13, in other words, at a timing during the operation of measuring blood pressure, a pulse rate is calculated using a pulse data that has a higher accuracy from the pressure pulse wave detected by the pressure sensor 23 and a photoelectric pulse wave detected by the artery volume sensor 30 when the signal level of the pressure pulse wave detected by the pressure sensor 23 that measures the inner pressure of the air bladder 13 is a reference level or above.

Here, as one example, determining which has higher accuracy, a signal to noise ratio of the pressure pulse wave detected by the pressure sensor 23 and a photoelectric pulse wave detected by the artery volume sensor 30 are calculated as signal levels, and the pulse rate is calculated by using the pulse wave information that has the higher signal to noise ratio. Generally, detection of a signal becomes possible when the level of a specified target signal is higher than the level of the surrounding noise signals. Accordingly, when the signal to noise ratio value of a signal is high, detection of the signal is easier and the measurement accuracy is higher. Conversely, when the signal to noise ratio value of a signal is low, detection of the signal is harder and the measurement accuracy is lower. As another example for determining which has higher accuracy, a pulse wave oscillation expressed by the signal may also be used.

Functional Configuration

Figure 7:
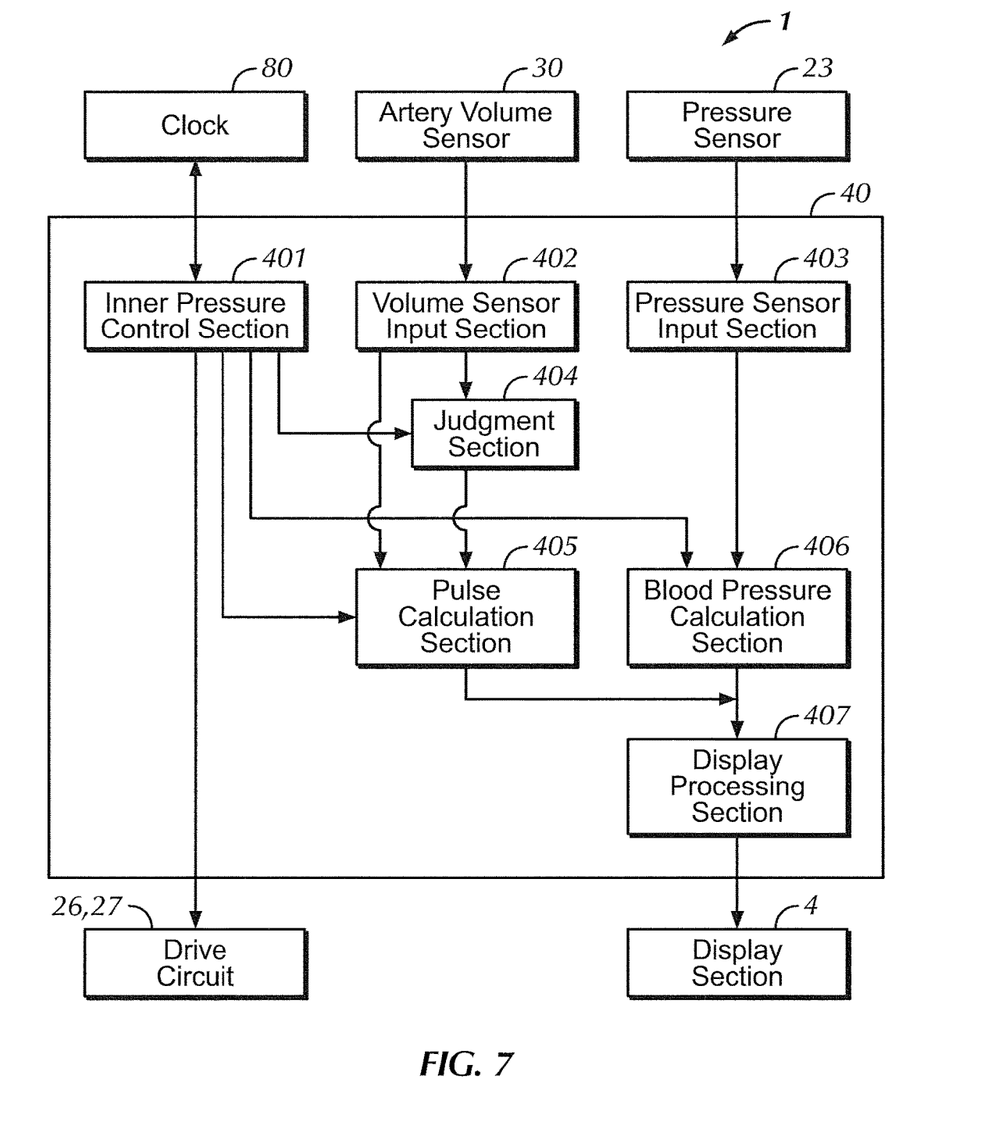
FIG. 7 is a block diagram illustrating a specific example of a functional configuration of the sphygmomanometer.

FIG. 7 is a block diagram illustrating a specific example of a functional configuration of the sphygmomanometer 1 in order to measure blood pressure and pulse. Each function illustrated in FIG. 7 is mainly formed on the CPU 40 by reading and carrying out a program stored in memory 6 by the CPU 40, and at least a portion may be realized by a hardware configuration such as the device configuration illustrated in FIG. 6 or an electric circuit.

Referring to FIG. 7, the CPU 40 includes an inner pressure control section 401 to carry out inner pressure control of the air bladder 13 at a timing that is predetermined in advance in reference to time by a clock 80, a volume sensor input section 402 to receive from the artery volume sensor 30 input of a sensor signal according to an artery volume, a pressure sensor input part 403 to receive from the pressure sensor 23 input of a sensor signal according to an inner pressure of the air bladder 13, a judgment section 404 to judge a sensor signal used for calculating pulse rate by using the signal to noise ratio of a sensor signal from the artery volume sensor 30 and a sensor signal from the pressure sensor 23 according to a timing of the inner pressure control in the inner pressure control section, a pulse calculation section 405 to calculate a pulse rate, a blood pressure calculation section 406 to calculate a blood pressure value, and a display processing section 407 to process display the calculation result on a display section 4 as the measurement result.

Operational Flow

Figure 8:
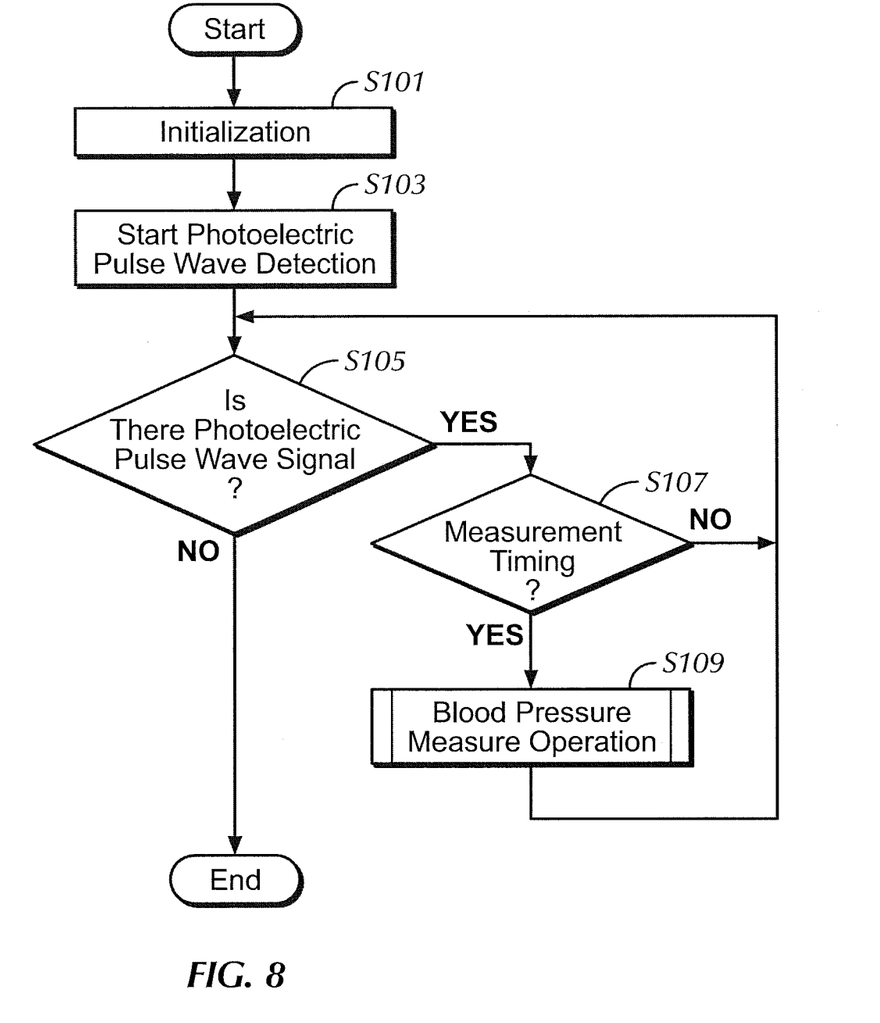
FIG. 8 is a flow diagram illustrating a flow for a measurement operation by the sphygmomanometer.

FIG. 8 is a flow diagram illustrating a flow of a measurement operation by the sphygmomanometer 1. The operation illustrated in the flow diagram in FIG. 8 is an operation that is started by turning on the power of the sphygmomanometer 1 by pushing down the power switch that is not illustrated but included in the operation section 3, the CPU 40 reads and carries out the program stored in the memory 6 to be realized by demonstrating each function illustrated in FIG. 7.

In reference to FIG. 8, when the sphygmomanometer 1 is turned on, the CPU 40 initializes a processing memory region of the CPU 40 in step S101, and carries out 0 mmHg correction of the pressure sensor by discharging the air within the air bladder for measurement as the initialization processing.

When the initialization is completed, the CPU 40 starts detecting a pulse wave based on a sensor signal from the artery volume sensor 30 in step S103. When the signal level is a predetermined reference value or higher (YES in step S105), it determines that the air bladder 13 is mounted properly in the measurement location (so that the artery volume sensor 30 is placed directly above an artery), and stands by until the start time of the operation for measuring blood pressure. The predetermined reference value here can be set at a level that can be measured without the pulse wave sensor signal being buried. If the air bladder is not mounted in an appropriate location, the signal may not be detected or only an extremely small sensor signal may be detected, and therefore the measurement by the artery volume sensor 30 becomes difficult.

When the signal level is below a predetermined reference value (NO in step S105), it determines that the air bladder 13 is not yet mounted or not mounted appropriately, and the series of operations are ended without carrying out the operation to measure blood pressure.

When reaching the start time of the operation to measure blood pressure (YES in step S107), the CPU 40 executes the operation to measure blood pressure in step S109. When not reaching the start time of the operation to measure blood pressure (NO in step S107), it goes back to the operation in step S105 to verify the signal level of the photoelectric pulse wave.

Figure 9:
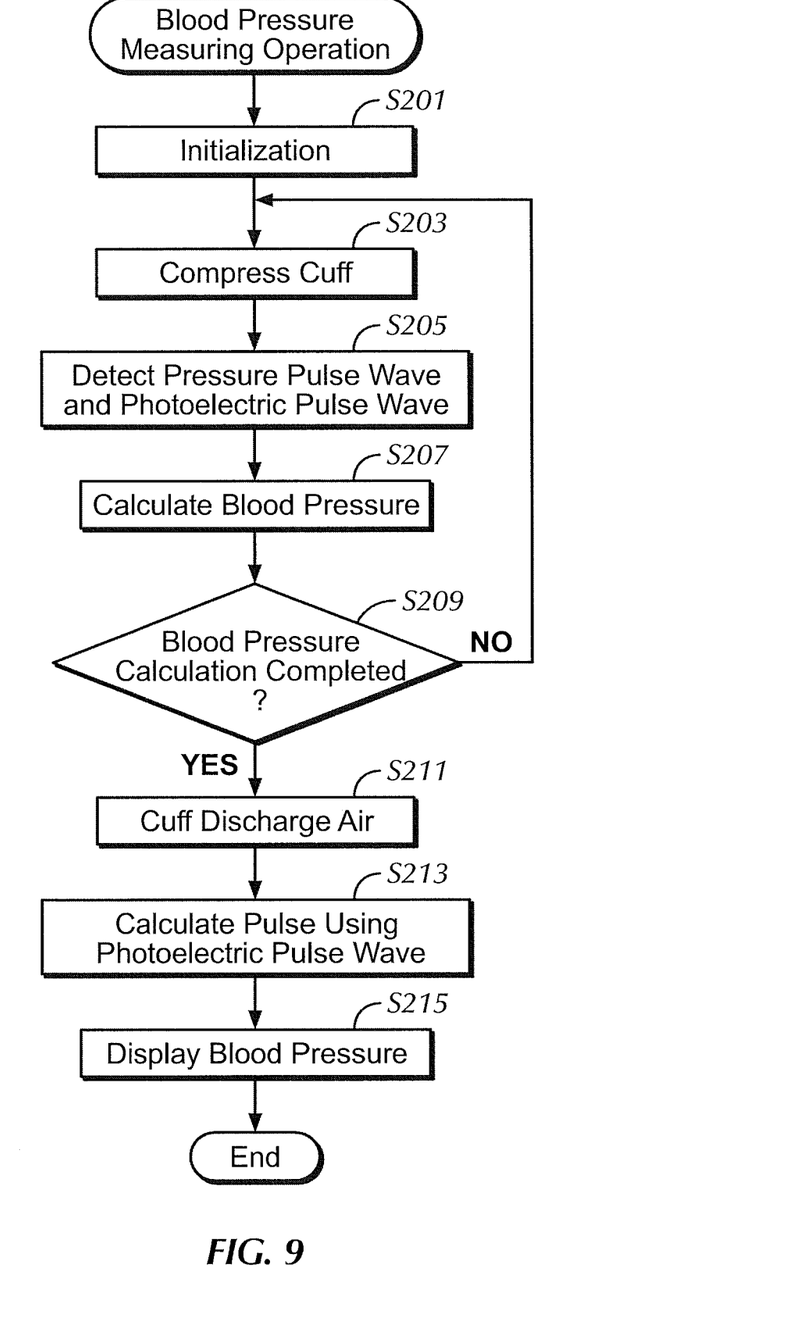
FIG. 9 is a flow diagram illustrating a specific flow of the blood pressure measurement operation in step S109 of FIG. 8.

FIG. 9 is a flow diagram illustrating a specific flow of the blood pressure measurement operation in step S109.

Referring to FIG. 9, the CPU 40 initializes the processing memory region of the CPU 40 as the initialization of the sphygmomanometer, and 0 mmHg correction of the pressure sensor is carried out by discharging the air within the air bladder 13 in step S201.

After the initialization process, the CPU 40 closes a valve 22 in step S203, and drives a pump 21 at a predetermined drive level. Accordingly, the air bladder 13 is compressed gradually.

In step S205, the CPU 40 carries out an operation for photoelectric pulse wave detection by the artery volume sensor 30 and the pressure pulse wave that extracts pressure variation associated with an artery volume change that is superimposed on the air bladder 13 while compressing the air bladder 13 gradually, and calculates the pulse. The details of the pulse calculation will be described later. Next, blood pressure is calculated by applying a predetermined algorithm to the pressure pulse wave signal in step S207. A conventional oscillometric method may be used for this method.

If the blood pressure is not yet calculated (YES in step S209), the operation returns to step S203, and the air bladder 13 is compressed gradually again.

When the blood pressure calculation is completed and the blood pressure value is determined (YES in step S209), the CPU 40 stops the drive of the pump 21 and opens the valve completely in step S211. Accordingly, the air within the air bladder is discharged. Further, the CPU 40, from then on, carries out the operation for detecting photoelectric pulse waves by the artery volume sensor 30 in step S213 to calculate pulse.

The CPU 40 displays a blood pressure value calculated in step S215.

Figure 10:
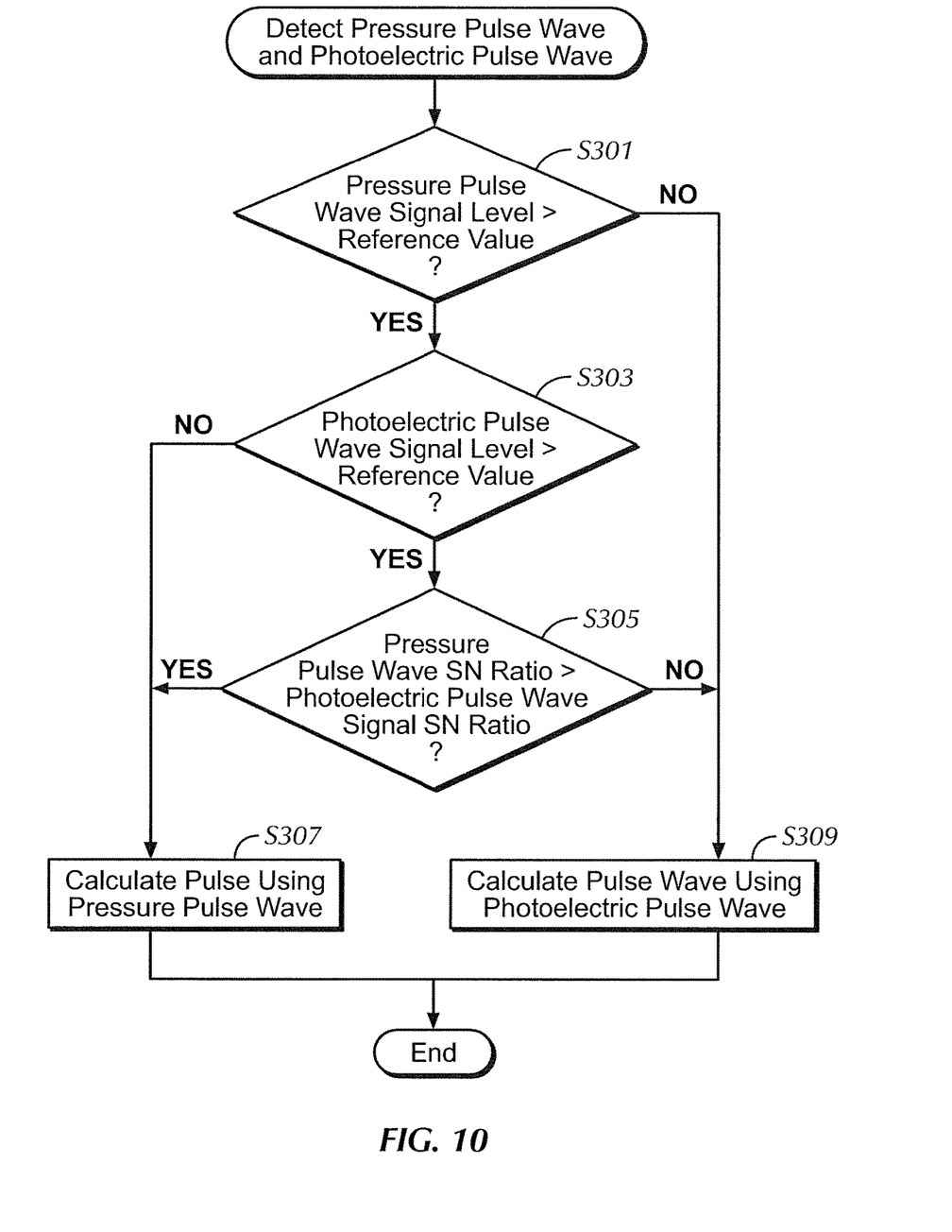
FIG. 10 is a flow diagram illustrating a specific flow of pulse calculation by a pressure pulse wave and a photoelectric pulse wave in step S205 of FIG. 9.

FIG. 10 is a flow diagram illustrating a specific flow of pulse calculation by a pressure pulse wave and a photoelectric pulse wave in step S205 of FIG. 9. In step S205, the CPU 40 determines whether the pulse can be calculated by comparing with the reference value to the signal level of the pressure pulse wave obtained from the pressure sensor 23, and the signal level of the photoelectric pulse wave obtained from the artery volume sensor 30. Furthermore, when the pulse can be calculated by using either one of the sensor signals, the CPU 40 determines the sensor signal having the higher accuracy as the sensor signal for using to calculate pulse.

More specifically, referring to FIG. 10, the CPU 40 compares the signal level of the pressure pulse wave obtained from the pressure sensor 23 and the reference value stored in advance. When the signal level of the pressure pulse wave is below the reference value (NO in step S301), the CPU 40 determines to use the sensor signal from the artery volume sensor 30 for calculating the pulse rate, and calculates the pulse rate using the photoelectric pulse wave in step S309.

When the signal level of the pressure pulse wave is the reference value or higher (YES in step S301), the CPU 40 further compares the signal level of the photoelectric pulse wave obtained from the artery volume sensor 30 and the reference value stored in advance. When the signal level of the photoelectric pulse wave is below the reference value (NO in step S303), the CPU 40 determines to use the sensor signal from the pressure sensor 23 for calculating the pulse rate, and calculates the pulse rate using the pressure pulse wave in step S307.

When the signal level of the photoelectric pulse wave is the reference value or higher (YES in step S303), the CPU 40 determines to use the sensor signal having a higher accuracy for calculating the pulse rate. As an example, the CPU 40 calculates SN ratio from each of the sensor signals (step S305), determines to use the sensor signal having the higher SN ratio for calculating the pulse rate, and calculates the pulse rate using the sensor signal (steps S307 and S309). As another example, CPU 40 may determine to use the sensor signal that more greatly exceeds the signal level from the reference value for calculating the pulse rate using the comparison in steps S301 and S303. Further, a parameter other than the SN ratio may be used.

Advantageous Efficacy of Embodiments

As previously described, when particularly the air bladder 13 during the operation for measuring blood pressure is deformed, there may be a case in which the positional relationship and orientation with the measurement location as illustrated in FIG. 5 change depending on the arrangement of the artery volume sensor 30. As a result, there may be a case in which the pulse wave is not detected accurately as illustrated in FIGS. 2 through 4.

In contrast, particularly while the air bladder 13 is deformed during the operation for measuring blood pressure, the pulse wave is detected using either one of the sensor signals that satisfies the reference value between the signal level of the sensor signal from the pressure sensor 23 and the signal level of the sensor signal from the artery volume sensor 30 by carrying out the operation described above by the sphygmomanometer 1. Furthermore, these signal levels are compared to each other when both satisfy the reference value, and the pulse wave is detected using the sensor signal that has the higher signal level, in other words, that which has the higher accuracy, and then, the pulse is calculated.

Accordingly, pulse wave detection with high accuracy is achievable even when the artery is compressed by the air bladder 13, and the pulse rate can be calculated accurately.

Another Example 5

In addition, although the method for calculating blood pressure in the example above uses the oscillometric method, the calculation method is not limited to this method, and the method may be Korotkoff sounds, a volume oscillometric method, or other blood pressure calculation methods. Further, a method for calculating blood pressure at the time of reducing the pressure may be used instead of a method for calculating the blood pressure at the time of compression.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An electronic sphygmomanometer for measuring a blood pressure and a pulse rate, comprising:
    a cuff comprising an air bladder for wrapping around a measurement location of a patient;
    a pressure sensor mounted on the cuff that measures an inner pressure of the air bladder;
    an artery volume sensor mounted on the cuff that detects a pulse wave signal of the patient based on a change of volume of an artery;
    a processor connected to the pressure sensor and the artery volume sensor that is programmed to calculate the blood pressure and the pulse rate based on the signal received from the pressure sensor and the artery volume sensor, the processor being further programmed to:
        increase or decrease the inner pressure of the air bladder at a predetermined timing;
        receive the pulse wave signal detected by the artery volume sensor;
        receive a pressure pulse wave signal, which is superimposed on the inner pressure of the air bladder and detected by the pressure sensor;
        choose only one of the detected pulse wave signal and the detected pressure pulse wave signal as a signal for calculating the pulse rate of the patient in accordance with a predetermined method during a period when the inner pressure of the air bladder is increased or decreased,
            wherein the predetermined method comprises:
                comparing the detected pressure pulse wave signal with a first predetermined reference value,
                wherein if the detected pressure pulse wave signal is below the first predetermined reference value, the detected pulse wave signal is the chosen signal, and
                wherein if the detected pressure pulse wave signal is above the first predetermined reference value, comparing the detected pulse wave signal with a second predetermined reference value,
                wherein if the detected pulse wave signal is below the second predetermined reference value, the detected pressure pulse wave signal is the chosen signal, and
                wherein if the detected pulse wave signal is above the second predetermined reference value, comparing a signal to noise ratio of the detected pressure pulse wave signal with a signal to noise ratio of the detected pulse wave signal to determine the chosen signal,
                wherein if the signal to noise ratio of the detected pressure pulse wave signal is greater than the signal to noise ratio of the detected pulse wave signal, the detected pressure pulse wave signal is the chosen signal, and
                wherein if the signal to noise ratio of the detected pulse wave signal is greater than the signal to noise ratio of the detected pressure pulse wave signal, the detected pulse wave signal is the chosen signal;
        calculate the pulse rate of the patient based on the chosen signal; and
        calculate the blood pressure based on the received pressure pulse wave signal.

2. The electronic sphygmomanometer according to claim 1, wherein the processor is further programmed to choose the signal having a higher signal to noise ratio as the chosen signal for calculating the pulse rate of the patient as a result of comparing the signal to noise ratio of the detected pressure pulse wave signal with the signal to noise ratio of the detected pulse wave signal.

3. The electronic sphygmomanometer according to claim 1, wherein the artery volume sensor is a photoelectronic sensor.

4. The electronic sphygmomanometer according to claim 1, wherein the artery volume sensor is an impedance sensor.

5. The electronic sphygmomanometer according to claim 1, wherein the electronic sphygmomanometer is a wrist sphygmomanometer that measures the blood pressure and the pulse rate on a wrist of the patient.

6. A method of measuring a blood pressure and a pulse rate of a patient comprising:
    wrapping a cuff comprising an air bladder around an arm of a patient, wherein the cuff is provided with a pressure sensor that measures an inner pressure of the air bladder and an artery volume sensor that detects a volume of an artery;
    detecting a pulse wave signal by using the artery sensor based on a change of the volume of the artery;
    inflating and deflating the air bladder to measure the blood pressure and detecting a pressure pulse wave signal by using the pressure sensor based on a change of the inner pressure of the air bladder, which is superimposed on the inner pressure of the air bladder during the inflation and deflation;
    choosing only one of the detected pulse wave signal and the detected pressure pulse wave signal as a signal for calculating the pulse rate of the patient in accordance with a predetermined method during the inflation and deflation of the air bladder, wherein the predetermined method comprises:
    providing the processor of claim 1,
        comparing the detected pressure pulse wave signal with a first predetermined reference value,
        wherein if the detected pressure pulse wave signal is below the first predetermined reference value, the detected pulse wave signal is the chosen signal, and
        wherein if the detected pressure pulse wave signal is above the first predetermined reference value, comparing the detected pulse wave signal with a second predetermined reference value, wherein if the detected pulse wave signal is below the second predetermined reference value, the detected pressure pulse wave signal is the chosen signal, and wherein if the detected pulse wave signal is above the second predetermined reference value, comparing a signal to noise ratio of the detected pressure pulse wave signal with a signal to noise ratio of the detected pulse wave signal to determine the chosen signal, wherein if the signal to noise ratio of the detected pressure pulse wave signal is greater than the signal to noise ratio of the detected pulse wave signal, the detected pressure pulse wave signal is the chosen signal, and wherein if the signal to noise ratio of the detected pulse wave signal is greater than the signal to noise ratio of the detected pressure pulse wave signal, the detected pulse wave signal is the chosen signal; and calculating the pulse rate of the patient based on the signal chosen during the inflation and deflation of the air bladder.

7. The method according to claim 6, further comprising comparing a signal to noise ratio value of the pulse wave signal and a signal to noise ratio value of the pressure pulse wave signal, and choosing the signal having a higher signal to noise ratio value for calculating pulse rate of the patient.

8. The method according to claim 6, wherein the artery volume sensor is a photoelectronic sensor.

9. The method according to claim 6, wherein the artery volume sensor is an impedance sensor.

10. The method according to claim 6, wherein the electronic sphygmomanometer is a wrist sphygmomanometer that measures the blood pressure and the pulse rate on a wrist of the patient.

* * * * *